(12) United States Patent
Quan et al.

(10) Patent No.: US 11,452,852 B2
(45) Date of Patent: Sep. 27, 2022

(54) APPLICATOR FOR WATER-SOLUBLE SHEET-SHAPED PREPARATION

(71) Applicant: COSMED PHARMACEUTICAL CO., LTD., Kyoto (JP)

(72) Inventors: Ying-Shu Quan, Kyoto (JP); Ying-Zhe Li, Kyoto (JP); Kiyotsune Higuchi, Kyoto (JP); Hiroshi Tanaka, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 279 days.

(21) Appl. No.: 16/494,184

(22) PCT Filed: Mar. 28, 2018

(86) PCT No.: PCT/JP2018/012726
§ 371 (c)(1),
(2) Date: Sep. 13, 2019

(87) PCT Pub. No.: WO2018/181466
PCT Pub. Date: Oct. 4, 2018

(65) Prior Publication Data
US 2020/0376243 A1  Dec. 3, 2020

(30) Foreign Application Priority Data

Mar. 28, 2017 (JP) .............................. JP2017-063899

(51) Int. Cl.
*A45D 34/04* (2006.01)
*B05B 11/00* (2006.01)
(Continued)

(52) U.S. Cl.
CPC .......... *A61M 35/003* (2013.01); *A45D 34/04* (2013.01); *B05B 11/3001* (2013.01);
(Continued)

(58) Field of Classification Search
CPC .............. A45D 34/04; A45D 2200/056; A45D 2200/1027; A45D 34/00; A45D 40/26;
(Continued)

(56) References Cited

U.S. PATENT DOCUMENTS 2,186,140 A *  1/1940  Kurtz ...................... A47L 13/22
                                                         401/186
5,567,073 A    10/1996  de Laforcade et al.
(Continued)

FOREIGN PATENT DOCUMENTS

DE  20 2004 018 315 U1  4/2005
FR       2 894 941 A1   6/2007
(Continued)

OTHER PUBLICATIONS

Written Opinion of the International Searching Authority (PCT/ISA/237) for Application No. PCT/JP2018/012726 dated May 1, 2018 (English Translation mailed Oct. 10, 2019).
(Continued)

*Primary Examiner* — David J Walczak
(74) *Attorney, Agent, or Firm* — Cheng Law Group, PLLC

(57) ABSTRACT

A nozzle having at least one hole on an end portion having a plane with a size capable of holding a sheet-like water-soluble preparation. The nozzle also has concave-convex portions on a portion of the plane excluding the hole. An applicator for a sheet-like water-soluble preparation which is composed of a liquid container and the nozzle.

12 Claims, 5 Drawing Sheets

(51) Int. Cl.
  *A61M 35/00* (2006.01)
  *A61M 37/00* (2006.01)
(52) U.S. Cl.
  CPC .................. *A45D 2200/056* (2013.01); *A45D 2200/1027* (2013.01); *A61M 2037/0023* (2013.01)
(58) Field of Classification Search
  CPC ... A45D 2200/10; B05B 11/3001; B05B 1/00; B05B 1/04; B05B 1/14; B05B 1/28; B05B 1/34; B05B 1/3405; A61M 35/003; A61M 2037/0023; A61M 35/006; A61M 35/00
  USPC ............................................ 401/28, 261–266
  See application file for complete search history.

(56) References Cited

U.S. PATENT DOCUMENTS

| | | | |
|---|---|---|---|
| 8,048,089 B2 * | 11/2011 | Ignon ................. | A61B 17/3205 606/131 |
| 2002/0087182 A1 | 7/2002 | Trautman et al. | |
| 2002/0091357 A1 | 7/2002 | Trautman et al. | |
| 2002/0123675 A1 | 9/2002 | Trautman et al. | |
| 2003/0198502 A1 * | 10/2003 | Maloney ................ | B65D 47/42 401/265 |
| 2004/0087893 A1 | 5/2004 | Kwon | |
| 2004/0199103 A1 | 10/2004 | Kwon | |
| 2005/0096586 A1 | 5/2005 | Trautman et al. | |
| 2005/0100391 A1 * | 5/2005 | Dobbs .................... | A47L 13/26 401/188 R |
| 2005/0148926 A1 | 7/2005 | Trautman et al. | |
| 2005/0234401 A1 | 10/2005 | Trautman et al. | |
| 2005/0251088 A1 | 11/2005 | Kwon | |
| 2005/0261631 A1 | 11/2005 | Clarke et al. | |
| 2006/0074376 A1 | 4/2006 | Kwon | |
| 2006/0095061 A1 | 5/2006 | Trautman et al. | |
| 2006/0142691 A1 | 6/2006 | Trautman et al. | |
| 2006/0276731 A1 | 12/2006 | Thiebaut et al. | |
| 2007/0020038 A1 * | 1/2007 | Tani .................... | B05C 17/0133 401/265 |
| 2007/0027427 A1 | 2/2007 | Trautman et al. | |
| 2007/0156124 A1 | 7/2007 | Ignon et al. | |
| 2009/0177171 A1 | 7/2009 | Ignon et al. | |
| 2012/0123387 A1 | 5/2012 | Gonzalez et al. | |
| 2014/0364801 A1 | 12/2014 | Trautman et al. | |
| 2015/0025459 A1 | 1/2015 | Kimmel et al. | |
| 2015/0272850 A1 | 10/2015 | Yoneto et al. | |
| 2015/0367117 A1 | 12/2015 | Ross et al. | |
| 2016/0074644 A1 | 3/2016 | Cao et al. | |
| 2016/0082242 A1 | 3/2016 | Burton et al. | |
| 2018/0110970 A1 | 4/2018 | Burton et al. | |
| 2018/0304063 A1 | 10/2018 | Gonzalez et al. | |
| 2019/0134369 A1 | 5/2019 | Ross et al. | |

FOREIGN PATENT DOCUMENTS

| | | |
|---|---|---|
| JP | 6-126217 A | 5/1994 |
| JP | 2004-510530 A | 4/2004 |
| JP | 2004-510534 A | 4/2004 |
| JP | 2004-510535 A | 4/2004 |
| JP | 2005-533625 A | 11/2005 |
| JP | 2006-500973 A | 1/2006 |
| JP | 2007-509706 A | 4/2007 |
| JP | 2011-78711 A | 4/2011 |
| JP | 2011-194189 A | 10/2011 |
| JP | 2013-500773 A | 1/2013 |
| JP | 2014-24828 A | 2/2014 |
| JP | 2014-42788 A | 3/2014 |
| JP | 2015-165140 A | 9/2015 |
| JP | 20163-511679 A | 4/2016 |
| JP | 2016-523115 A | 8/2016 |
| JP | 2017-185162 A | 10/2017 |
| WO | WO-2011/006009 A1 | 1/2011 |

OTHER PUBLICATIONS

Supplementary European Search Report for the Application No. EP 18 774 734.0 dated Dec. 3, 2020.
International Search Report for the Application No. PCT/JP2018/012726 dated May 1, 2018.
Written Opinion of the International Searching Authority (PCT/ISA/237) for Application No. PCT/JP2018/012726 dated May 1, 2018.
The First Office Action for the Application No. 201880019472.8 from The State Intellectual Property Office of the People's Republic of China dated Apr. 30, 2021.

* cited by examiner

[FIG. 1]
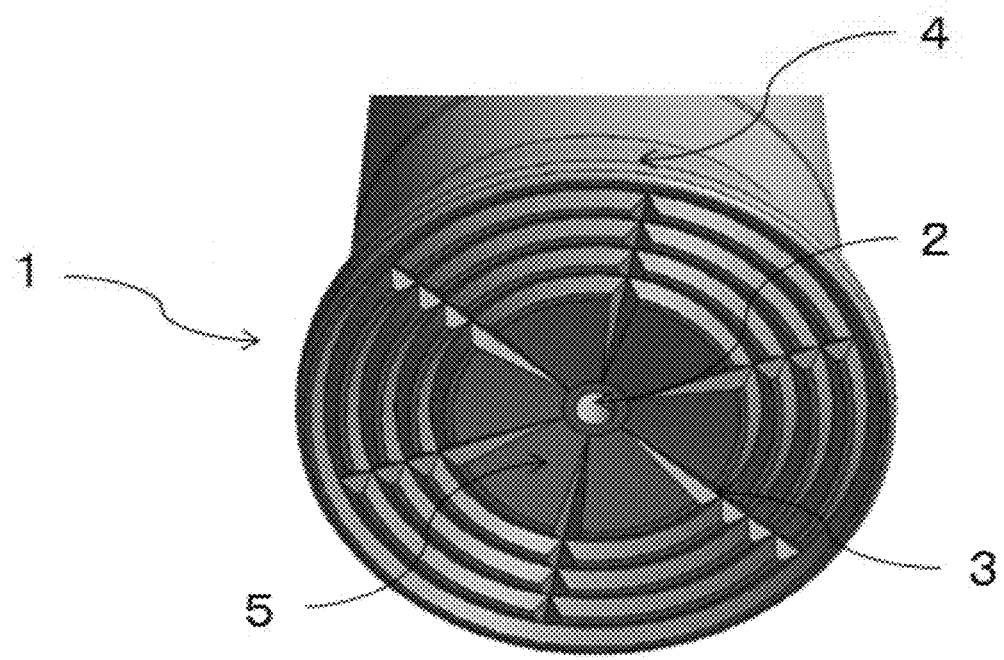

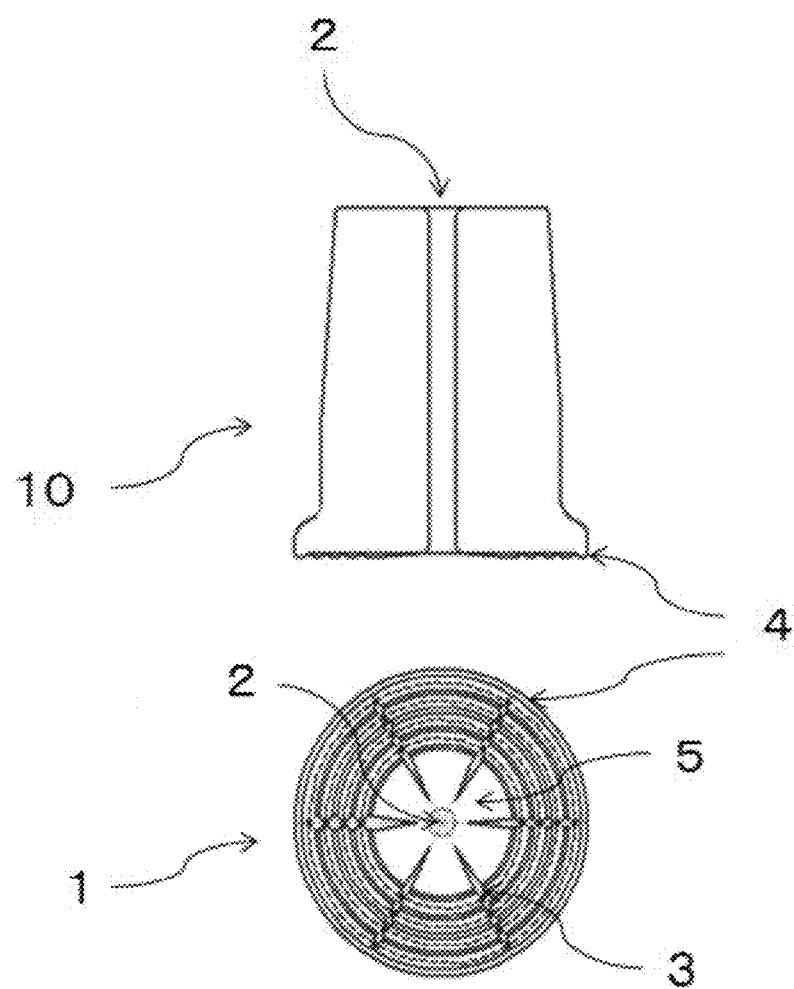
[FIG. 2]

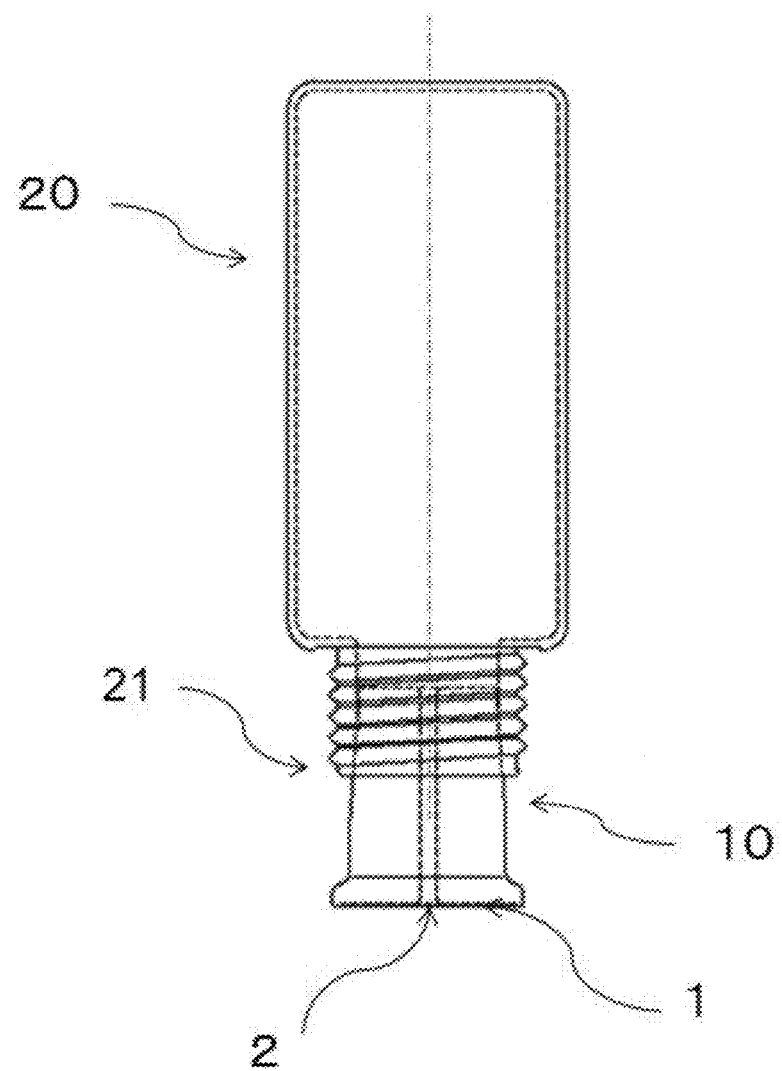
[FIG. 3]

[FIG. 4]
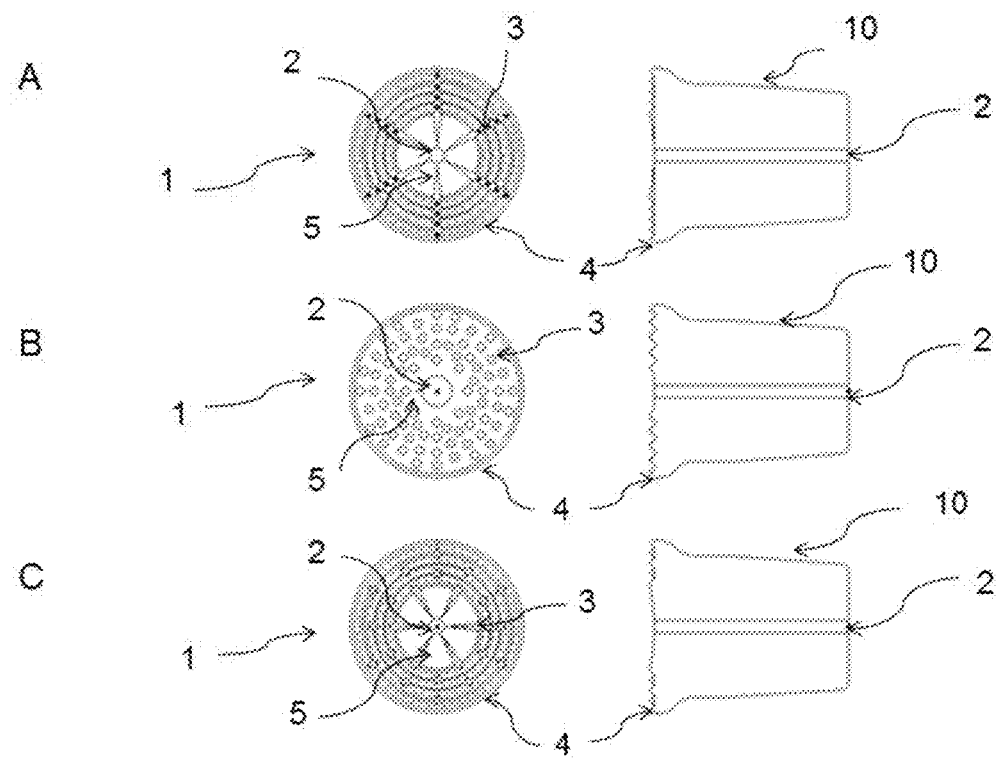
[FIG. 5]
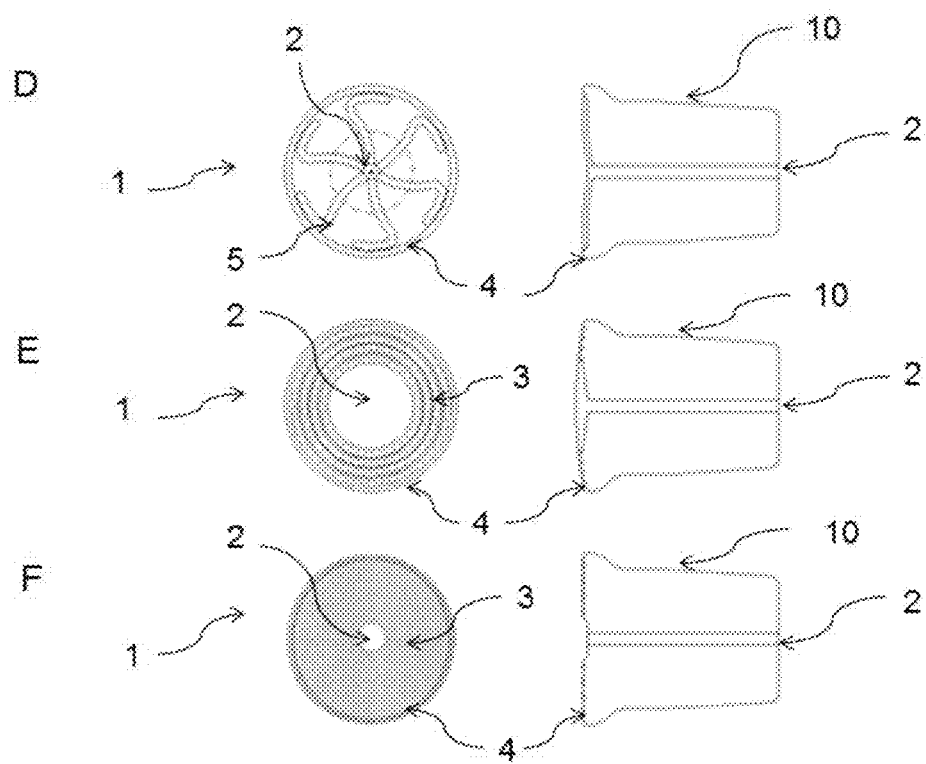

[FIG. 6]
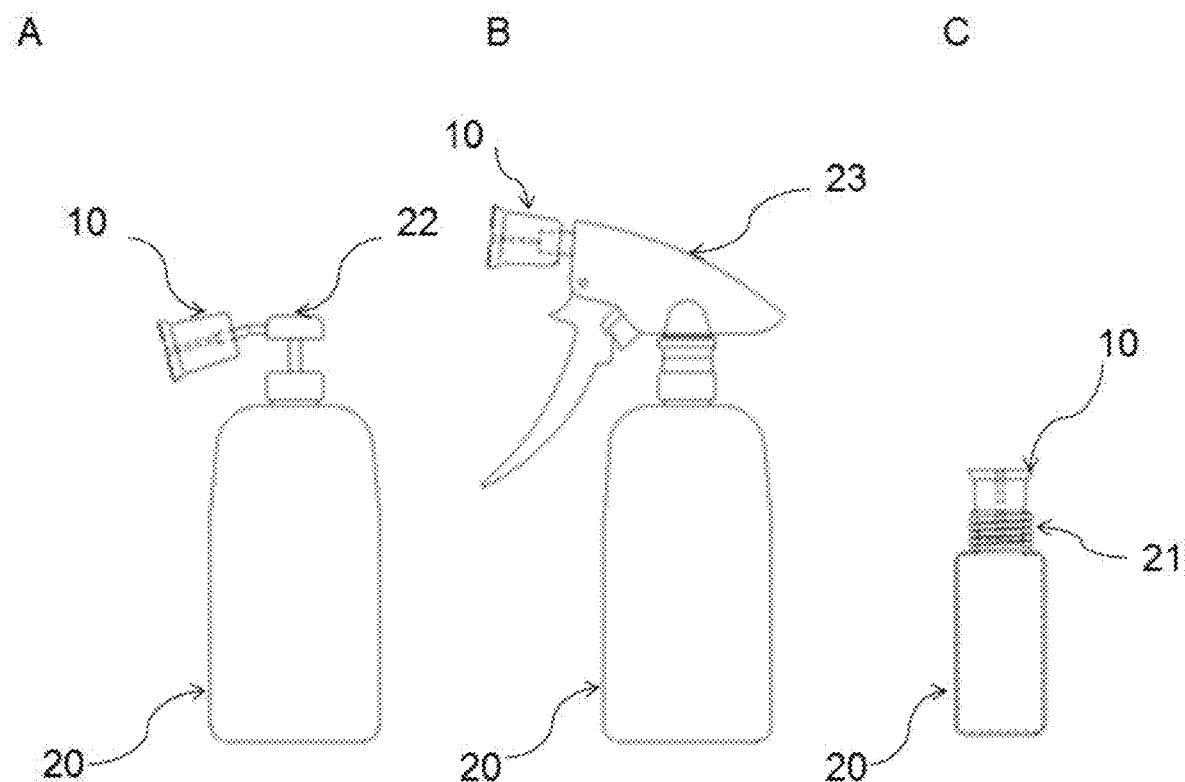

APPLICATOR FOR WATER-SOLUBLE SHEET-SHAPED PREPARATION

TECHNICAL FIELD

The present invention relates to an applicator nozzle for applying a sheet-like water soluble preparation to a skin, and an applicator equipped with the nozzle.

BACKGROUND ART

As a method of administering a drug to a human body, oral administration and transdermal administration are often used. Although injection is a typical transdermal administration method, it is troublesome and painful. In transdermal administration, skin stratum corneum works as a barrier to drug permeation, so only applying the drug on a skin surface does not necessarily cause enough permeability. In contrast, perforation of the corneum by using a minute needle, i.e. a microneedle can remarkably improve drug permeation efficiency compared to the application method. An article in which a large number of the microneedles are integrated on a substrate is a microneedle array. Furthermore, a product in which sheets such as an adhesive sheet for adhering the microneedle array to a skin or a protective release sheet for protecting and supporting the adhesive sheet when applying the microneedle array to a skin are added to the microneedle array in order to facilitate its use is called a microneedle patch.

When administering a microneedle array to a skin, it is not easy to insert microneedles into the skin only by pressing the microneedle array with a finger. This is because the skin is generally a soft and elastic tissue, and thus even if the pointed tips of the microneedles are pressed against the skin, the skin absorbs the impact and deforms to prevent the microneedles from entering the skin.

It is appropriate to impact the microneedle array in a direction to the skin for administering the microneedle array to the impact-absorbable skin. As specific methods for administering the microneedle array, microneedle administration devices (microneedle applicator) using a spring (Patent Documents 1 to 6, and 8), an air pressure (Patent Document 5), a magnetic force (Patent Document 7), and the like, have been proposed so far. For facilitating use of a spring even for women and children, ingenuity is required for a spring compression method and a trigger method. In addition, it is not necessarily easy to use the air pressure and the magnetic force. The conventional microneedle array administration devices still have practical problems, and the users have demanded a simpler device which can achieve reliable insertion.

Although microneedles made of a water-soluble material dissolve in water in a skin after insertion, this dissolution takes a lot of time and thus remarkably impairs convenience for recipients particularly in a case that the microneedles are intended for cosmetics. A microneedle array is prepared using a water-soluble material and inserted into a skin, to which subsequently water is supplied from the back side of the microneedle, and then the microneedles rapidly dissolve (Patent Document 9). In addition, the present inventors have developed a cosmetic hyaluronic acid gel sheet composed of a water-soluble polymer hyaluronic acid as a raw material, and have reported that the sheet is applied to a skin, to which subsequently a small amount of water is added, and the skin is massaged to enhance permeation of the hyaluronic acid and ingredients to the skin (Patent Document 10).

PRIOR ART DOCUMENTS

Patent Documents

Patent Document 1: Japanese Unexamined Patent Application No. 2004-510530 (Japanese Patent No. 4198985)
Patent Document 2: Japanese Unexamined Patent Application No. 2004-510534 (Japanese Patent No. 4104975)
Patent Document 3: Japanese Unexamined Patent Application No 2004-510535 (Japanese Patent No. 4659332)
Patent Document 4: Japanese Unexamined Patent Application No. 2005-533625
Patent Document 5: Japanese Unexamined Patent Application No. 2006-500973
Patent Document 6: Japanese Unexamined Patent Application No. 2007-509706 (Japanese Patent No. 4682144)
Patent Document 7: Japanese Patent Application Laid-Open No. 2011-078711
Patent Document 8: Japanese Patent Application Laid-Open No. 2014-42788
Patent Document 9: Japanese Patent Application Laid-Open No. 2011-194189 (Japanese Patent No. 5408592)
Patent Document 10: Japanese Patent Application Laid-Open No. 2014-024828 (Japanese Patent No. 5840107)

SUMMARY OF INVENTION

Problem to be Solved

The microneedle array and the cosmetic gel sheet composed of a water-soluble polymer as a raw material are sheet-like flexible preparations having a thickness of about several hundred μm for improving adhesiveness to a skin. When such a sheet-like water-soluble preparation is applied to the skin, the preparation absorbs moisture on a fingertip and adheres to the finger rather than the target skin, or when the preparation is applied to a scalp, adhesiveness is inhibited by hairs, and thus the preparation peels off before absorbed from the scalp, in some cases.

The problem to be solved by the present invention is to provide a means which makes it possible to reliably administer a sheet-like water-soluble preparation to skins at various sites and supply water from a back side of the sheet-like water-soluble preparation.

Herein, the sheet-like water-soluble preparation in the present invention includes not only a microneedle array but also a sheet-like preparation like a cosmetic water-soluble gel sheet, intended to be rapidly dissolved in water after application to the skin and percutaneously absorbed. The sheet-like water-soluble preparation is prepared using a water-soluble polymer as a base and has a thickness of about 1 mm or less. Examples of the water-soluble polymer include hyaluronic acid (or a sodium salt thereof) and a derivative thereof, collagen, hydroxypropylcellulose, chondroitin sulfate, dextran, proteoglycan, etc. and a mixture thereof. The back side of the sheet-like water-soluble preparation refers to a side opposite to the side in close contact with the skin.

Solution to Problem

The present inventors have conducted extensive studies in order to solve the above problem, and as a result, they have succeeded in developing a nozzle which facilitates adhesion and detachment of the sheet-like water-soluble preparation. Furthermore, the present inventors have completed a device which makes it possible to instantly apply the sheet-like water-soluble preparation to a skin and dissolve the preparation by attaching such a nozzle to various liquid containers.

The present invention is as follows.

[1] A nozzle having at least one hole on an end portion having a plane with a size capable of holding a sheet-like water-soluble preparation, and having concave-convex portions on a portion of the plane excluding the hole.

[2] The nozzle according to [1], wherein a depth of the concave-convex portions is 0.1 to 3.0 mm.

[3] The nozzle according to [1] or [2], wherein the concave-convex portions form grooves extending from the hole toward a peripheral edge of the end portion.

[4] The nozzle according to any one of [1] to [3], wherein the peripheral edge of the end portion is surrounded by a convex portion higher than the concave-convex portions.

[5] The nozzle according to any one of [1] to [4], which is made of a synthetic resin selected from a group consisting of a polyethylene resin, a polypropylene resin, a polyurethane resin, a polyvinyl chloride, and a silicone resin.

[6] An applicator for a sheet-like water-soluble preparation, which is composed of a liquid container and the nozzle according to any one of [1] to [5].

[7] The applicator according to [6], wherein the nozzle is attached to an opening of the liquid container.

[8] The applicator according to [6] or [7], wherein the sheet-like water-soluble preparation is held on the end portion of the nozzle so as to be applied to the skin, and a liquid is supplied to a back side of the preparation by pressing the liquid container.

[9] The applicator according to [6], wherein the liquid container is equipped with a spray device, and the nozzle is attached to an end opening of the spray device.

[10] The applicator according to [9], wherein the sheet-like water-soluble preparation is held on the end portion of the nozzle so as to be applied to the skin, and the liquid is supplied to the back side of the preparation by discharge from the spray device.

[11] The applicator according to [6], wherein the liquid container is equipped with a pump, and the nozzle is attached to an end opening of the pump.

[12] The applicator according to [11], wherein the sheet-like water-soluble preparation is held on the end portion of the nozzle so as to be applied to the skin, and the liquid is ejected to the back side of the preparation by pushing the pump.

Effects of Invention

The nozzle according to the present invention can rapidly dissolve the preparation by pressing the end of the nozzle against the sheet-like water-soluble preparation pasted on a skin and supplying water to the preparation from the hole of the nozzle. Since the end portion of the nozzle according to the present invention has the concave-convex portions, the dissolved preparation reliably stays on the skin side without adhering to the end portion of the nozzle. The end portion of the nozzle according to the present invention has the plane having the concave-convex portions, and thus in a case of a relatively small sheet-like water-soluble preparation, the preparation can be applied to the skin while held on the plane of the end portion. This case is hygienic because the preparation is not directly handled with hands.

The applicator according to the present invention is composed of the nozzle according to the present invention and the liquid container, and any liquid container may be used as long as the opening of the liquid container can be fitted into the nozzle. When a water-soluble microneedle array is administered using the applicator according to the present invention, the end of the nozzle is pressed against the microneedle array and left for an appropriate time to ensure insertion of the microneedles to the skin. Furthermore, the end of the nozzle is pressed against the microneedle array to uniformly supply water from the liquid container to the entire surface of the back side of the array, so that the microneedle array can rapidly dissolve. When the cosmetic water-soluble gel sheet is applied using the applicator according to the present invention, the end of the nozzle is pressed against the gel sheet, and water in the liquid container is supplied from the back side, so that the gel sheet rapidly dissolves and spreads over the skin surface to enhance moisture retention of the skin and absorption of valuable components.

BRIEF DESCRIPTION OF DRAWINGS

FIG. 1 illustrates an example of a shape of a nozzle end portion.

FIG. 2 illustrates a sectional view and a bottom view of the nozzle in Example 1.

FIG. 3 illustrates an applicator in which the nozzle in Example 1 is attached to a liquid container made of polyethylene.

FIG. 4 illustrates examples (A, B, C) of the nozzle, wherein each left side shows a bottom view, and each right side shows a sectional view.

FIG. 5 illustrates other examples (D, E, F) of the nozzle, wherein each left side shows a bottom view, and each right side shows a sectional view.

FIG. 6 illustrates examples (A, B, C) of the applicator in which the nozzle is attached to various liquid containers having openings.

DESCRIPTION OF EMBODIMENTS

The nozzle according to the present invention is a water supply member intended to dissolve the sheet-like water-soluble preparation. The end portion of the nozzle has the plane with a size capable of holding the sheet-like water-soluble preparation. For the nozzle according to the present invention, the shape of the plane of the end portion can be changed depending on the size of the sheet-like water-soluble preparation, and may be a circle, an oval, a comma shape, a polygon such as triangle, square, pentagon and hexagon. The main body of the nozzle according to the present invention may have a cylinder shape, an elliptic cylinder shape, or a polygonal pillar shape in accordance with the shape of the plane of the end portion. The cylinder shape is desirable for fitting the nozzle into openings of various liquid containers.

The end portion of the nozzle according to the present invention has at least one hole. The number of the holes may be two or more for the purpose of introducing water from the liquid container to the back side of the sheet-like water-soluble preparation, and also the size of the hole is not particularly limited. The hole may be positioned at the center or the peripheral portion of the plane of the end portion. Also, the arrangement and interval of the plurality of holes are not particularly limited.

The concave-convex portions are formed on the plane of the end portion of the nozzle according to the present invention excluding the holes. The concave-convex portions are of any shapes such as a helical shape, a dot shape and a radial shape as long as the sheet-like water-soluble preparation can be attached to or detached from the end portion of the nozzle and grooves capable of supplying water over the entire end portion from the hole can be formed. In relation to the degree of the concave and convex, typically the concave and convex have depths of desirably 0.1 to 3.0 mm, more preferably 0.1 to 2.0 mm. If the depth is 0.1 mm or less, the rapidity is impaired in supplying water to the surface through the hole. If the depth is 3.0 mm or more, the amount of water supplied over the entire surface through the hole needs to be large.

The area ratio of the convex portions or flat portions to the groove portions or concave portions is desirably 20:1 or higher. If the area ratio of the concave portions is too small, the groove portions are small, and it is difficult to supply water over the entire bottom surface. If the area of the groove portions is too large, the plane of the nozzle flat portion is small, and even if the water-soluble sheet is pressed against the skin by the nozzle, the adhesiveness with the flat portion is insufficient, resulting in possibility of insufficient adhesion to the nozzle. Thus, the area ratio of the convex portions or flat portions to the groove portions or concave portions is desirably 1:10 or lower.

It is desirable that the peripheral edge of the end portion of the nozzle according to the present invention is surrounded by a convex portion higher than the aforementioned concave-convex portions so that supplied water does not overflow. The convex portion on the peripheral edge plays a role of a weir such that water spread through the grooves formed by the concave-convex portions is prevented from overflowing to the outside of the sheet-like water-soluble preparation.

The nozzle according to the present invention desirably has grooves in which the concave-convex portions extend from the hole toward the peripheral edge of the end portion for the purpose of smoothly supplying an appropriate amount of water to the entire sheet-like water-soluble preparation. Herein, the groove refers to a lower part formed by adjacent two convex portions and one concave portion surrounded by the two convex portions. The shape of the groove is not particularly limited. Specific examples of the grooves include concentrical elongated grooves on the concave-convex portions 3 concentrically spreading around a hole 2 at the center, and radial (flabellate) grooves 5 directly connected to the hole 2, on the end portion of the nozzle shown in FIG. 1. This nozzle has a convex portion 4 on the peripheral edge.

FIG. 4 and FIG. 5 illustrate further aspects of the nozzle according to the present invention. In FIG. 4A and FIG. 4C, the radial grooves 5 and concentrical grooves are formed. In FIG. 4B, the concave-convex portions 3 are formed of many dots, and the grooves 5 made of the dots are formed from the hole 2 toward the peripheral edge. In FIG. 5D, helical grooves 5 are formed from the hole 2 toward the peripheral edge. In FIG. 5E, a large hole 2 is formed at the center, and concentrical grooves 5 are formed around the hole 2. In FIG. 5F, fine concave-convex portions 3, which are mesh-like grooves invisible to the naked eye, are formed over the entire plane excluding the hole 2.

Materials of the nozzle according to the present invention are not particularly limited, and various materials such as metal, ceramic and plastic can be used. Considering easiness of manufacture, convenience in use and the like, plastic is preferable, and particularly, a polyolefin resin such as a polyethylene resin and a polypropylene resin, and a synthetic resin such as a polyvinyl chloride, a polyurethane resin and a silicone resin are more preferable. Considering fittability of various materials with the liquid container and goodness in contact feeling of the nozzle to the skin, a soft polymer material is preferable. As a measure for a hardness of the nozzle material, a Young's modulus is desirably 500 Pa to 5 MPa. As a specific material, a soft polyolefin resin, a polyurethane resin and a silicone resin are preferable, and the silicone resin is more preferable.

A nozzle made of a synthetic resin can be manufactured by a known method, e.g. a molding method by injecting a raw material resin into a mold.

The applicator according to the present invention is composed of a liquid container and the nozzle according to the present invention. The liquid container and the nozzle may be in a combination in which they are separated. In this case, the nozzle is attached to the opening of the liquid container during use. In the liquid container, a liquid may be previously charged, or the liquid may be injected immediately before use. In the present invention, the liquid is typically water, but may be a mixture liquid with a solvent other than water as long as the sheet-like water-soluble preparation can be dissolved. In addition, the liquid may be an aqueous solution additionally containing medicinal ingredients and valuable ingredients to be applied to the skin as needed.

The material for the liquid container is not particularly limited, and various materials such as metal, ceramic and plastic can be used in consideration of the fittability with the nozzle. Considering easiness of manufacture, convenience in use, and the like, plastic is preferable, and particularly, a polyolefin resin such as a polyethylene resin and a polypropylene resin, and a synthetic resin such as a polyvinyl chloride, a polyurethane resin and a silicone resin are more preferable.

The applicator according to the present invention has the nozzle according to the present invention. The applicator is e.g. an applicator shown in FIG. 6C. In this case, the sheet-like water-soluble preparation is held on the end portion of the nozzle so as to be applied to the skin, and the liquid can be supplied to a back side of the preparation by pressing the liquid container. The amount of the liquid to be supplied can be appropriately set depending on the size (area, thickness) or the like of the sheet-like water-soluble preparation. The amount of the liquid can be regulated depending on a size of the hole of the nozzle, a pressure applied to the liquid container, a frequency of pressings, or the like.

When the liquid container is equipped with a spray device, the nozzle is attached to an end opening of the spray device in the applicator according to the present invention. The applicator is e.g. an applicator shown in FIG. 6B. Also in this case, similarly the sheet-like water-soluble preparation is held on the end portion of the nozzle so as to be applied to the skin, and the liquid can be supplied to the back side of the preparation by discharge from the spray device. The amount of the liquid to be supplied can be appropriately set depending on the size (area, thickness) or the like of the sheet-like water-soluble preparation. The amount of the liquid can be regulated depending on a size of the hole of the nozzle, dischargeability of the spray device, a frequency of discharges, or the like.

When the liquid container is equipped with a pump, the nozzle is attached to an end opening of the pump in the applicator according to the present invention. The applicator is e.g. an applicator shown in FIG. 6A. Also in this case, similarly the sheet-like water-soluble preparation is held on the end portion of the nozzle so as to be applied to the skin, and the liquid can be ejected to the back side of the preparation by pushing the pump. The amount of the liquid to be ejected can be appropriately set depending on the size (area, thickness) or the like of the sheet-like water-soluble preparation. The amount of the liquid can be regulated depending on a size of the hole of the nozzle, dischargeability of the pump, a frequency of ejections, or the like.

As described above, in the present invention, various liquid containers are attached with the nozzle according to the present invention in a form that can be fitted into the opening of the liquid container, to provide various forms of applicators. Thus, the nozzle and the liquid container can be freely combined depending on the shape, the application purpose, the application frequency, the application site, or the like of the sheet-like water-soluble preparation. In addition, the nozzle according to the present invention can be inexpensively mass-produced, and therefore, for use, the nozzle can be changed for each subject and each application day. After use, the nozzle is detached from the applicator, the opening of the applicator is sealed with a cap or the like, the liquid remaining in the liquid container is stored under refrigeration, and can be used again within an expiration date. Furthermore, the applicator according to the present invention can also be used as a single-use disposable device by attaching the nozzle to the liquid container charged with a single dose of the liquid.

Hereinafter, embodiments of the present invention will be explained based on Examples. However, the present invention is not limited to contents of Examples.

EXAMPLES

Example 1

A nozzle as shown in FIG. 1 was prepared. The nozzle was prepared by mold injection using a silicone resin (one liquid type RTV rubber, manufactured by Shin-Etsu Chemical Co., Ltd.). On a plane of a nozzle end 1, a diameter was 12 mm, a depth of concentrical concave-convex portions 3 was 0.5 mm, and an interval between the concave-convex portions was 1 mm. The upper diagram of FIG. 2 shows a sectional view of the entire nozzle, and the lower diagram of FIG. 2 shows a bottom view of the nozzle. The hole 2 penetrates a center of a nozzle main body 10 and can be seen at the center of the end portion. The liquid flows out of the hole 2, spreads over the grooves 5, and further spreads over the entire plane through the concave-convex portions 3.

This nozzle was attached to a polyethylene container (see FIG. 3), 0.1 g of LIMUVEIL HV (1.2% fucoidan-containing aqueous solution, manufactured by TANGLEWOOD) was dissolved in 200 g of water, and the fucoidan-containing extract was charged in the container to prepare an applicator.

The microneedle patch was manufactured as follows. To 90 g of water, 5 g of hyaluronic acid (FCH-80, originating from culture, manufactured by Kikkoman Biochemifa Company) and 5 g of LIMUVEIL HV were added, to prepare a homogeneous solution. The aqueous solution was cast on a mold, dried at room temperature for 24 hours, and removed from the mold to obtain a microneedle array sheet. The sheet was cut into a microneedle array having a diameter of 1 cm. A fucoidan content per one microneedle was 25 µg. This microneedle patch and the extract are preparations intended for hair growth.

Prior to use, the back side of the microneedle array was pressed, pasted and held by the applicator nozzle portion. The array was pressed against a forehead of a volunteer, and the container was pushed to supply the fucoidan extract from the back side of the microneedle array. When the applicator was removed after 1.5 minutes, the microneedle array was dissolved on the skin. The microneedle array sheet did not remain in the applicator nozzle portion.

In a case of a microneedle array containing a hair grower, an application site has hairs, and thus the array hardly adheres to the skin only by press with a finger or the like. Using the applicator according to the present invention, the microneedle array rapidly dissolves (in a very short time) while pressing the microneedle array against the skin. The microneedle array is pressed by the applicator until the array dissolves, so that the hair grower can be reliably delivered into the skin.

Comparative Example 1

The same test as in Example 1 was carried out using a nozzle having a flat bottom surface without concaves and convexes (the outer shape is the same as in Example 1). The fucoidan extract was supplied from the back side of the microneedle array by pushing the container. When the applicator was removed after 1.5 minutes, the microneedle array adhered to the bottom surface of the nozzle, furthermore the bottom surface could not be uniformly wetted by water, and therefore the microneedle array insufficiently dissolved.

Comparative Example 2

The microneedle array was pasted to a forehead of a volunteer, then the back side of the array was covered with a medical tape to hold the array on the skin. In this case, it took 3 hours to dissolve the needle portion.

REFERENCE NUMERALS 1 end portion of nozzle
2 hole
3 concave-convex portion
4 convex portion on peripheral edge
5 groove
10 nozzle main body
20 liquid container
21 opening of liquid container
22 pump
23 spray device

The invention claimed is:

1. A nozzle having at least one hole on an end portion having a plane with a size capable of holding a sheet-like water-soluble preparation, and having concave-convex portions on a portion of the plane excluding the hole,
   wherein a depth of the concave-convex portions is 0.1 to 3.0 mm.

2. The nozzle according to claim 1, wherein the concave-convex portions form grooves extending from the hole toward a peripheral edge of the end portion.

3. The nozzle according to claim 1, wherein a peripheral edge of the end portion is surrounded by a convex portion higher than the concave-convex portions.

4. The nozzle according to claim 1, wherein the nozzle is made of a synthetic resin selected from a group consisting of a polyethylene resin, a polypropylene resin, a polyurethane resin, a polyvinyl chloride, and a silicone resin.

5. An applicator for a sheet-like water-soluble preparation, wherein the applicator is composed of a liquid container and the nozzle according to claim 1.

6. The applicator according to claim 5, wherein the nozzle is attached to an opening of the liquid container.

7. The applicator according to claim 5, wherein the sheet-like water-soluble preparation is held on the end portion of the nozzle so as to be applied to the skin, and a liquid is supplied to a back side of the preparation by pressing the liquid container.

8. The applicator according to claim 5, wherein the liquid container is equipped with a spray device, and the nozzle is attached to an end opening of the spray device.

9. The applicator according to claim 8, wherein the sheet-like water-soluble preparation is held on the end portion of the nozzle so as to be applied to the skin, and the liquid is supplied to the back side of the preparation by discharge from the spray device.

10. The applicator according to claim 5, wherein the liquid container is equipped with a pump, and the nozzle is attached to an end opening of the pump.

11. The applicator according to claim 10, wherein the sheet-like water-soluble preparation is held on the end portion of the nozzle so as to be applied to the skin, and the liquid is ejected to the back side of the preparation by pushing the pump.

12. The nozzle according to claim 1, wherein the plane of the end portion is perpendicular to a path formed by the at least one hole.

\* \* \* \* \*